United States Patent
Sinivaara

(10) Patent No.: US 8,224,286 B2
(45) Date of Patent: Jul. 17, 2012

(54) RADIO COMMUNICATION DEVICE

(75) Inventor: Hasse Sinivaara, San Jose, CA (US)

(73) Assignee: Savox Communications Oy AB (Ltd), Espoo (FI)

( * ) Notice: Subject to any disclaimer, the term of this patent is extended or adjusted under 35 U.S.C. 154(b) by 171 days.

(21) Appl. No.: 12/594,100

(22) PCT Filed: Mar. 30, 2007

(86) PCT No.: PCT/FI2007/000078
§ 371 (c)(1),
(2), (4) Date: Mar. 5, 2010

(87) PCT Pub. No.: WO2008/119866
PCT Pub. Date: Oct. 9, 2008

(65) Prior Publication Data
US 2010/0151921 A1    Jun. 17, 2010

(51) Int. Cl.
*H04M 11/04* (2006.01)
(52) U.S. Cl. .................. 455/404.1; 340/539.26
(58) Field of Classification Search .................. 455/501, 455/41.2, 575.2, 574; 381/72, 94.1, 106; 340/539.26
See application file for complete search history.

(56) References Cited

U.S. PATENT DOCUMENTS

| | | | | |
|---|---|---|---|---|
| 5,594,735 A * | 1/1997 | Jokura | ........................... | 370/337 |
| 5,794,199 A * | 8/1998 | Rao et al. | ...................... | 704/258 |
| 6,070,140 A | 5/2000 | Tran | | |
| 6,516,068 B1 * | 2/2003 | Ciurpita et al. | ................ | 381/106 |
| 7,342,502 B2 * | 3/2008 | Harkins et al. | .............. | 340/573.1 |
| 2002/0164013 A1 * | 11/2002 | Carter et al. | .............. | 379/387.02 |
| 2002/0198708 A1 * | 12/2002 | Zak et al. | ....................... | 704/233 |
| 2003/0092394 A1 * | 5/2003 | Gray et al. | .................... | 455/67.4 |
| 2003/0173829 A1 | 9/2003 | Zeng | | |
| 2003/0224778 A1 | 12/2003 | Oosawa | | |
| 2006/0009970 A1 | 1/2006 | Harton | | |
| 2006/0140416 A1 * | 6/2006 | Berg | ............................... | 381/72 |

FOREIGN PATENT DOCUMENTS

| | | |
|---|---|---|
| CH | 681841 | 11/1990 |
| GB | 2182568 | 9/1986 |
| GB | 2421443 | 6/2006 |
| GB | 2415316 | 12/2006 |
| JP | 6097867 | 4/1994 |
| JP | 7022994 | 1/1995 |
| JP | 2007089061 | 5/2007 |
| WO | 0007157 | 2/2000 |
| WO | 0041065 | 7/2000 |
| WO | 2004018013 | 3/2004 |

OTHER PUBLICATIONS

International Search Report dated Dec. 3, 2007 in PCT application.

* cited by examiner

*Primary Examiner* — Tu X Nguyen
(74) *Attorney, Agent, or Firm* — Young & Thompson

(57) ABSTRACT

The invention relates to a method and arrangement for reducing power consumption of a radio communication device. In a solution according to the invention an audio signal is monitored (801) and the radio communication devise is activated to transmit (802) a radio signal containing information of the audio signal only when (803) the audio signal contains speech. The power consumption of the radio communication device can be reduced without a need for manual control actions that could limit the freedom of action of a person who is using of the radio communication device.

24 Claims, 9 Drawing Sheets

RADIO COMMUNICATION DEVICE

FIELD OF THE INVENTION

The invention relates to a radio communication device, and more particularly, to a method and arrangement for reducing power consumption of a radio communication device. The invention further relates to a breathing protection apparatus comprising a radio communication device.

BACKGROUND

A breathing mask can be equipped with or connected to a portable radio communication device in order to enable the wearer of the breathing mask to communicate with other persons. For example, a fire fighter wearing a breathing mask has to be able to communicate with other fire fighters of his team and with fire chiefs. Solutions in which a breathing mask is equipped with a radio communication device are described, for example, in publications GB2415316 and GB2421443. Power consumption of a radio communication device is a critical issue, because a battery that energizes the radio communication device should be as light and small as possible and, on the other hand, it might cause even a dangerous situation if the electrical energy stored in the battery runs out at a critical time instant and the wearer of the breathing masks is no longer able to communicate.

A radio communication device consumes power especially when transmitting a radio signal. In one solution according to the prior art, a transmission of a radio signal is constantly active and, therefore, the average power consumption of the radio communication device is very high. During a significant portion of time, the radio signal carries only such voice components that are typically of no use, e.g. breathing noise, pressurised air ventilation, and external noise. Furthermore, in conjunction with certain radio protocols, the transmission of the above-mentioned useless voice components causes unintentional reservation of protocol units as time slots, data frames, or data packets.

In another solution according to the prior art, a transmitter of a radio communication device is "push-to-talk" activated and coupled via an corded link to an control box that comprises a push button. In this case, a transmission of a radio signal is not constantly active and, therefore, the average power consumption of the radio communication device is reduced. A user of the radio communication device must push a button when talking into a microphone in order to allow the radio transmission. This requires that the user can have only one hand free while talking into the microphone. For example, for a fire fighter it is highly important that freedom of action is not excessively limited during communication, i.e. both hands should be free for other purposes also during communication. Furthermore, the control box can often frustrate the user as it may limit the action of freedom also when there is no communication or it has to be placed to a pocket or some other suitable place when not used.

SUMMARY

In accordance with a first aspect of the invention, there is provided a new arrangement for reducing power consumption of a radio communication device. The arrangement is characterized in that it comprises a control unit arranged to monitor an audio signal and to activate the radio communication device to transmit a radio signal containing information of said audio signal as a response to a situation in which said audio signal is detected to contain speech.

In accordance with a second aspect of the invention, there is provided a new radio communication device. The radio communication device is characterized in that it comprises a control unit arranged to monitor an audio signal and to activate the radio communication device to transmit a radio signal containing information of said audio signal as a response to a situation in which said audio signal is detected to contain speech.

In accordance with a third aspect of the invention, there is provided a new breathing protection apparatus. The breathing protection apparatus comprises:
   a breathing mask, and
   a radio communication device capable of transmitting a radio signal containing information of an audio signal that is measured in the breathing mask.

The breathing protection apparatus is characterized in that it further comprises a control unit arranged to monitor said audio signal and to activate the radio communication device to transmit said radio signal as a response to a situation in which said audio signal is detected to contain speech of a wearer of the breathing protection apparatus.

In accordance with a fourth aspect of the invention, there is provided a new method for reducing power consumption of a radio communication device. The method is characterized in that it comprises:
   monitoring an audio signal, and
   activating the radio communication device to transmit a radio signal containing information of said audio signal as a response to a situation in which said audio signal is detected to contain speech.

A benefit provided by embodiments of the present invention when compared with prior art solutions of the kind described above is that power consumption of a radio communication device can be reduced without a need for manual control actions that could limit the freedom of action of a person who is using the radio communication device.

Various embodiments of the invention both as to constructions and to methods of operation, together with additional objects and advantages thereof, will be best understood from the following description of specific embodiments when read in connection with the accompanying drawings.

The embodiments of the invention presented in this document are not to be interpreted to pose limitations to the applicability of the appended claims. The verb "to comprise" is used in this document as an open limitation that does not exclude the existence of also unrecited features. The features recited in depending claims are mutually freely combinable unless otherwise explicitly stated.

BRIEF DESCRIPTION OF THE FIGURES

Embodiments of the invention presented in the sense of examples and their advantages are explained in greater detail below with reference to the accompanying drawings, in which.

DETAILED DESCRIPTION OF THE EMBODIMENTS

Figure 1A:
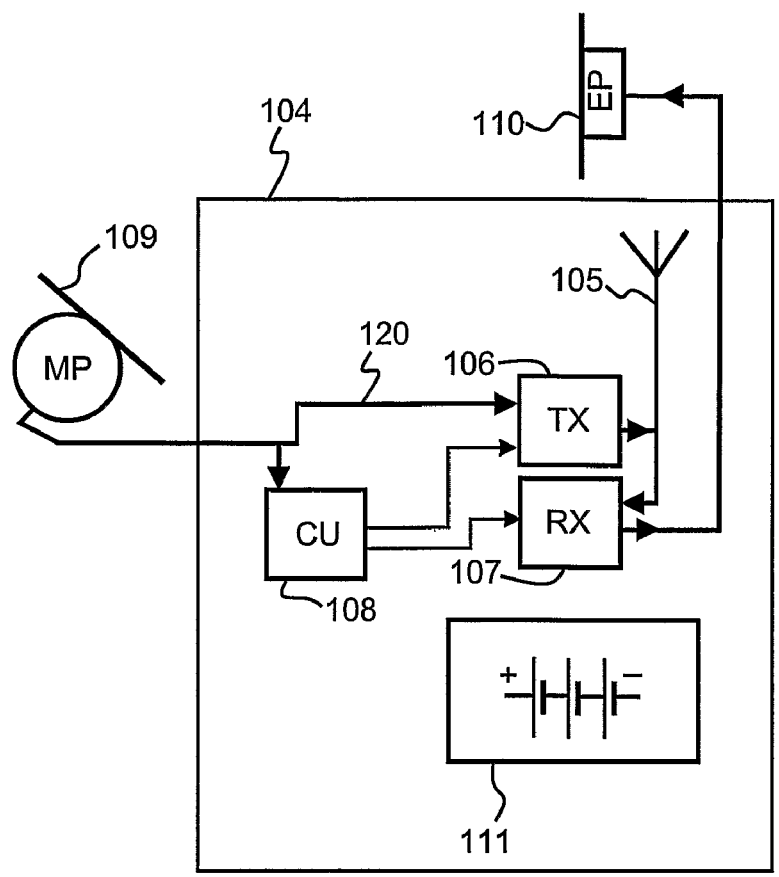
FIG. 1a shows a block diagram of a radio communication device that comprises an arrangement according to an embodiment of the invention for reducing power consumption of the radio communication device.

FIG. 1a shows a block diagram of a radio communication device 104 that comprises an arrangement according to an embodiment of the invention for reducing power consumption of the radio communication device. The radio communication device 104 comprises a radio transmitter (TX) 106, a radio receiver (RX) 107, and an antenna 105. The radio communication device 104 is connected to a microphone (MP) 109 arranged to transform voice into an electrical audio signal 120. The radio communication device 104 is connected to an earphone (EP) 110 arranged to transform an electrical audio signal into voice.

A control unit 108 represents the arrangement for reducing the power consumption of the radio communication device 104. The control unit 108 is arranged to monitor the electrical audio signal 120 measured with the microphone 109 and to activate the radio communication device 104 to transmit a radio signal containing information of the electrical audio signal 120 as a response to a situation in which the electrical audio signal 120 is detected to contain speech.

During a significant portion of time, the electrical audio signal 120 represents only such voice components that are typically of no use, e.g. breathing noise, pressurised air ventilation, and external noise. Furthermore, in conjunction with certain radio protocols, the transmission of the above-mentioned useless voice components would cause undesired reservation of protocol units as time slots, data frames, or data packets. The electrical power needed for transmitting the above-mentioned useless voice components is reduced and the undesired reservation of protocol units is at least partly avoided, because the radio communication device 104 is activated to transmit the radio signal containing information of the electrical audio signal 120 only when the electrical audio signal 120 is detected to contain speech.

The radio communication device comprises a battery element 111 that is arranged to energize the radio transmitter 106, the radio receiver, the microphone 109, the earphone 110, and the control unit 108.

In an arrangement according to an embodiment of the invention the control unit 108 is arranged to prevent the radio communication device 104 from transmitting any radio signals during time periods in which speech is not detected from the electrical audio signal 120. In an arrangement according to an alternative embodiment of the invention the control unit 108 is arranged to allow the radio communication device to transmit another radio signal during time periods in which the radio communication device is not activated to transmit the radio signal containing information of the electrical audio signal 120. The other radio signal can represent, for example, one or more of the following: a test signal for monitoring a radio link, a monitoring signal carrying measured data, and an update signal for a radio transceiver at a far end of the radio link. These signals can consist of bursts having short temporal durations. Therefore, these signals do not usually cause a significant contribution to a time average of the power consumption of the radio communication device 104. The test signal can be used for detecting e.g. a loss of connection in the radio link. The monitoring signal can be used for transferring e.g. a temperature measured from clothes of a fire fighter in order to avoid a situation in which the fire fighter might get a heat stroke. The update signal can be used e.g. for maintaining synchronization between the radio communication device 104 and the radio transceiver at the far end of the radio link.

There are numerous different algorithms and methods for detecting whether the electrical audio signal 120 contains speech. Some examples will be presented in this document, but any suitable method or algorithm known to a person skilled in the art can be used for detecting whether the electrical audio signal 120 contains speech.

In an arrangement according to an embodiment of the invention the control unit 108 comprises an adaptive speech detector that is taught to recognize at least one component of speech of a user of the radio communication device. The adaptive speech detector can be realized, for example, with a neural network or with an adaptive digital filter or with a combination thereof. The control unit 108 is arranged to regard a situation in which at least one component of speech of the user of the radio communication device is detected as the situation in which the electrical audio 120 signal is detected to contain speech.

In an arrangement according to an embodiment of the invention the control unit 108 comprises an analog band-pass filter arranged to attenuate frequency components of the electrical audio signal 120 that locate outside a frequency band of speech. For example, breathing noise has typically a spectrum that is different from that of speech. The electrical audio signal is an input signal of the analog band-pass filter. The control unit 108 is arranged to regard a situation in which level of an output signal of the analog band-pass filter exceeds a pre-determined threshold value as the situation in which the electrical audio 120 signal is detected to contain speech. The pre-determined threshold value can be, for example, zero. The pre-determined threshold value can be used for tuning the operation in order to achieve an acceptable balance between occurrence of situations in which speech is erroneously not detected (a missed detection) and occurrence of situations in which noise is erroneously regarded as speech (a false alarm of speech).

In an arrangement according to an embodiment of the invention the control unit 108 is arranged to switch the radio receiver 107 of the radio communication device 104 to a power saving mode as a response to the situation in which the electrical audio signal 120 contains speech. In the power saving mode the whole radio receiver 107 can be deactivated or certain pre-determined functions of the receiver can be deactivated in order to reduce the power consumption of the radio receiver.

In an arrangement according an embodiment of the invention the control unit 108 is arranged to receive the audio signal from a microphone that is located in a breathing mask of a breathing protection apparatus.

Figure 1B:
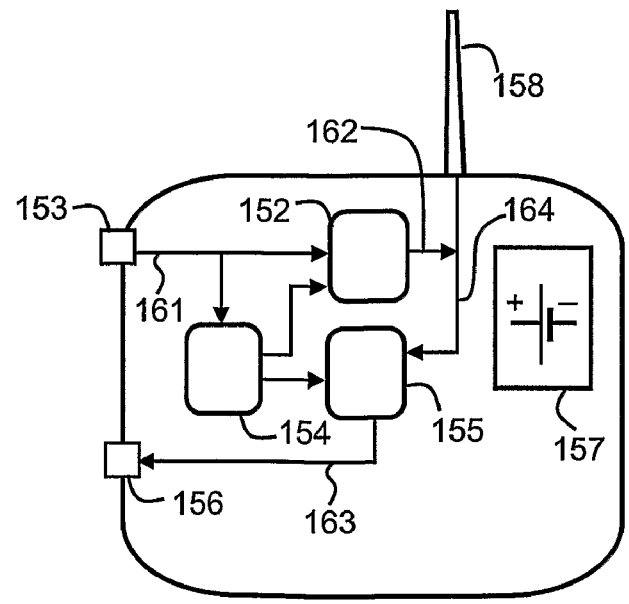
FIG. 1b shows a radio communication device according to an embodiment of the invention.

FIG. 1b shows a radio communication device according to an embodiment of the invention. The radio communication device comprises a control unit 154 arranged to monitor an audio signal 161 and to activate a radio transmitter 152 of the radio communication device to transmit a radio signal 162 containing information of the audio signal as a response to a situation in which the audio signal is detected to contain speech. The radio signal 162 is transmitted to a radio path via an antenna 158.

A radio communication device according to an embodiment of the invention comprises an electrical connector 153 for receiving the audio signal 161 from an external microphone that can be connected to the electrical connector 153. A radio communication device according to an alternative embodiment of the invention comprises an in-build microphone that is arranged to produce the audio signal 161.

A radio communication device according to an embodiment of the invention comprises a battery element 157 arranged to energize the radio communication device. A radio communication device according to an alternative embodiment of the invention comprises an electrical connector for receiving electrical energy from an external battery element.

A radio communication device according to an embodiment of the invention comprises a radio receiver 155 arranged to receive a radio signal 164 and to produce an audio signal 163. The radio communication device can comprise an electrical connector 156 for connecting the radio communication device to an external earphone or an external speaker device.

In a radio communication device according to an embodiment of the invention the control unit 154 is arranged to switch the radio receiver 155 of the radio communication device to a power saving mode as a response to the situation in which the audio signal 161 contains speech. In the power saving mode the whole radio receiver 155 can be deactivated or certain pre-determined functions of the receiver can be deactivated in order to reduce the power consumption of the radio receiver.

In a radio communication device according to an embodiment of the invention the radio transmitter 152 is capable of transmitting another radio signal during a time period in which the radio communication device is not activated to transmit the radio signal containing information of the audio signal. The other radio signal can represent one or more of the following: a test signal for monitoring a radio link, a monitoring signal carrying measured data, and an update signal for a transceiver at a far end of the radio link.

In a radio communication device according to an embodiment of the invention the radio transmitter 152 is arranged to transmit digital data to a radio path and the radio receiver 155 is arranged to receive digital data from the radio path. The radio transmitter can be adapted to use e.g. the quadrature amplitude modulation (QAM) line code or the carrierless amplitude and phase modulation (CAP) line code. Correspondingly, the radio receiver can be adapted to use e.g. the quadrature amplitude modulation (QAM) line code or the carrierless amplitude and phase modulation (CAP) line code.

A radio communication device according to an embodiment of the invention is arranged to support the Bluetooth® data transfer protocol.

A radio communication device according to an embodiment of the invention is arranged to support a data transfer protocol of a wireless local area network (WLAN).

A radio communication device according to an embodiment of the invention is arranged to support the WiMax data transfer protocol. The WiMax data transfer protocol is described e.g. in the IEEE 802.16 specification (Institute of Electrical and Electronics Engineers).

A radio communication device according to an embodiment of the invention is arranged to support both the Bluetooth® data transfer protocol and the data transfer protocol of a wireless local area network (WLAN).

In a radio communication device according an embodiment of the invention the control unit 154 is arranged to receive the audio signal 161 from a microphone that is located in a breathing mask of a breathing protection apparatus. The radio communication device can be, for example, physically integrated with the breathing mask of the breathing protection apparatus or the radio communication device can be connected to the breathing mask of the breathing protection apparatus via a corded link.

Figure 2:
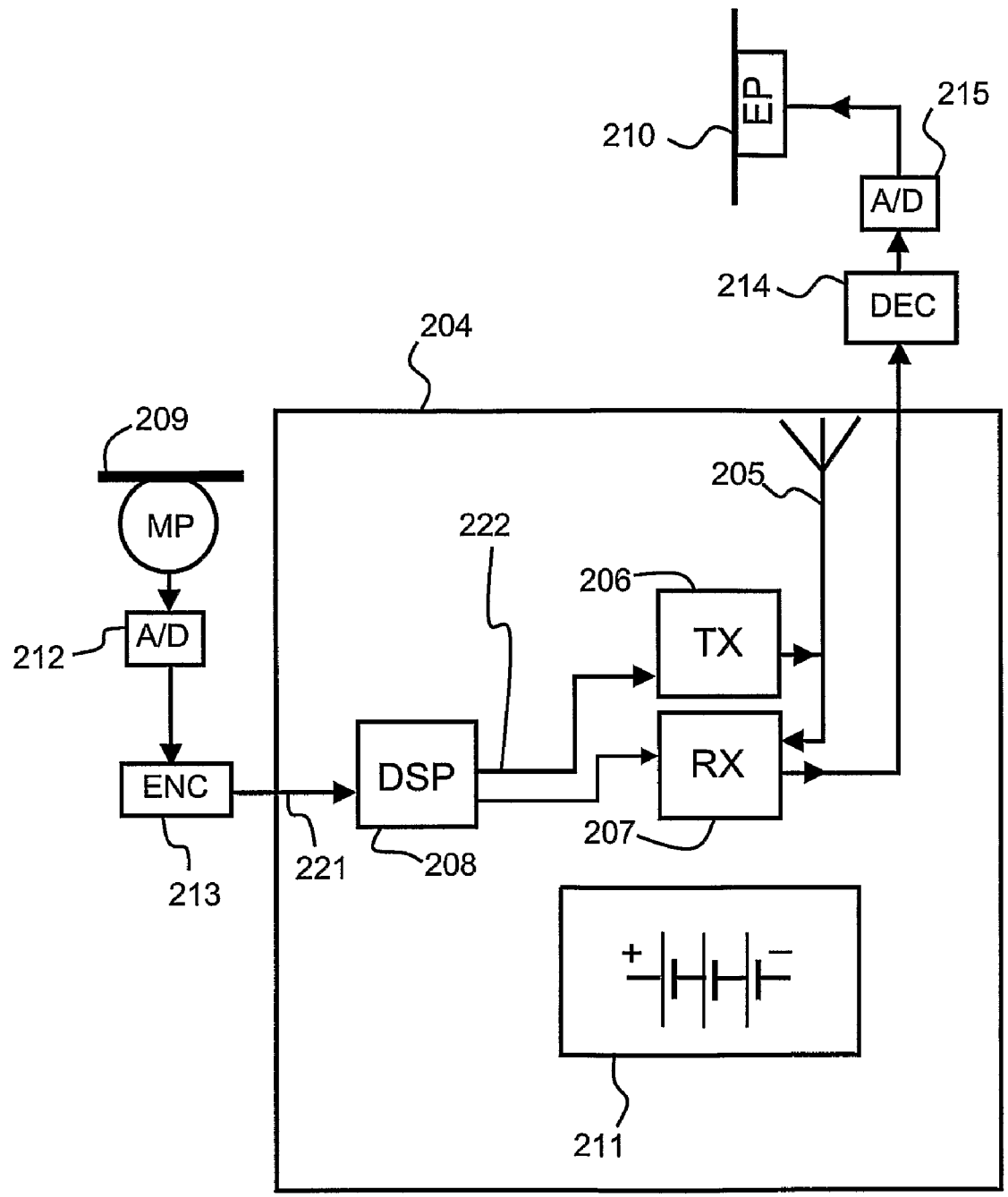
FIG. 2 shows a block diagram of a radio communication device that comprises an arrangement according to an embodiment of the invention for reducing power consumption of the radio communication device.

FIG. 2 shows a block diagram of a radio communication device that comprises an arrangement according to an embodiment of the invention for reducing power consumption of the radio communication device. The radio communication device 204 comprises a radio transmitter (TX) 206, a radio receiver (RX) 207, and an antenna 205. The radio communication device 204 is coupled to an earphone (EP) 210 via an audio decoder 214 (DEC) and a digital-to-analog converter 215 (D/A).

A control unit 208 that is a digital signal processor (DSP) represents the arrangement for reducing the power consumption of the radio communication device 204. The control unit 208 is arranged to monitor a digital audio signal 221 and to activate the radio communication device 204 to transmit a radio signal containing information of the digital audio signal 221 as a response to a situation in which the digital audio signal 221 is detected to contain speech. The digital audio signal 221 is produced with the microphone 209, with the analog-to-digital converter 212 (ND), and with an audio encoder (ENC) 213, i.e. the microphone 209, the analog-to-digital converter 212, and the audio encoder 213 act as a sensor for measuring the digital audio signal 221.

The radio communication device comprises a battery element 211 that is arranged to energize the radio transmitter 206, the radio receiver 207, the microphone 209, the analog-to-digital converter 212, the audio encoder 213, the audio decoder 214, the digital-to-analog converter 215, and the control unit 208.

In an arrangement according to an embodiment of the invention the control unit 208 is arranged to produce a processed audio signal 222 by attenuating signal components of the digital audio signal 221 other than speech. The signal components other than speech are typically noise. The control unit 208 is arranged to regard a situation in which level of the processed audio signal 222 exceeds a pre-determined threshold value as the situation in which the electrical audio signal contains speech. The pre-determined threshold value can be for example zero. The pre-determined threshold value can be used for tuning the operation in order to achieve an acceptable balance between occurrence of situations in which speech is erroneously not detected (a missed detection) and occurrence of situations in which noise is erroneously regarded as speech (a false alarm of speech).

There are numerous digital signal processing algorithms that can be used for attenuating the signal components of the digital audio signal 221 other than speech. Some examples are presented below, but any suitable algorithm known to a person skilled in the art can be used for attenuating the signal components of the digital audio signal 221 other than speech.

In an arrangement according to an embodiment of the invention the control unit 208 comprises a digital noise whitening filter (NWF). The digital audio signal 221 is an input signal of the digital noise whitening filter and a difference between the digital audio signal 221 and an output signal of the digital noise whitening filter is the processed audio signal 222 from which signal components other than speech have been attenuated.

In an arrangement according to an embodiment of the invention the control unit 208 comprises a digital band-pass filter (BPF) arranged to attenuate frequency components of the digital audio signal 221 that locate outside a frequency band of speech. The digital audio signal 221 is an input signal of the digital band-pass filter and an output signal of the digital band-pass filter is the processed audio signal 222 from which signal components other than speech have been attenuated.

In an arrangement according to an embodiment of the invention the control unit 208 comprises a digital noise whitening filter (NWF) and a digital band-pass filter (BPF). The digital band-pass filter and the digital noise whitening filter can be interconnected e.g. in the following way: the digital audio signal 221 is an input signal of the digital band-pass filter and an output signal of the digital band-pass filter is an input signal of the digital noise whitening filter. A difference between the output signal of the digital band-pass filter and an output signal of the digital noise whitening filter is the processed audio signal 222 from which signal components other than speech have been attenuated.

In an arrangement according to an embodiment of the invention the control unit 208 is arranged to switch the radio receiver 207 of the radio communication device 204 to a power saving mode as a response to the situation in which the digital audio signal 221 contains speech. In the power saving mode the whole radio receiver 207 can be deactivated or certain pre-determined functions of the receiver can be deactivated in order to reduce the power consumption of the radio receiver.

Figure 3:
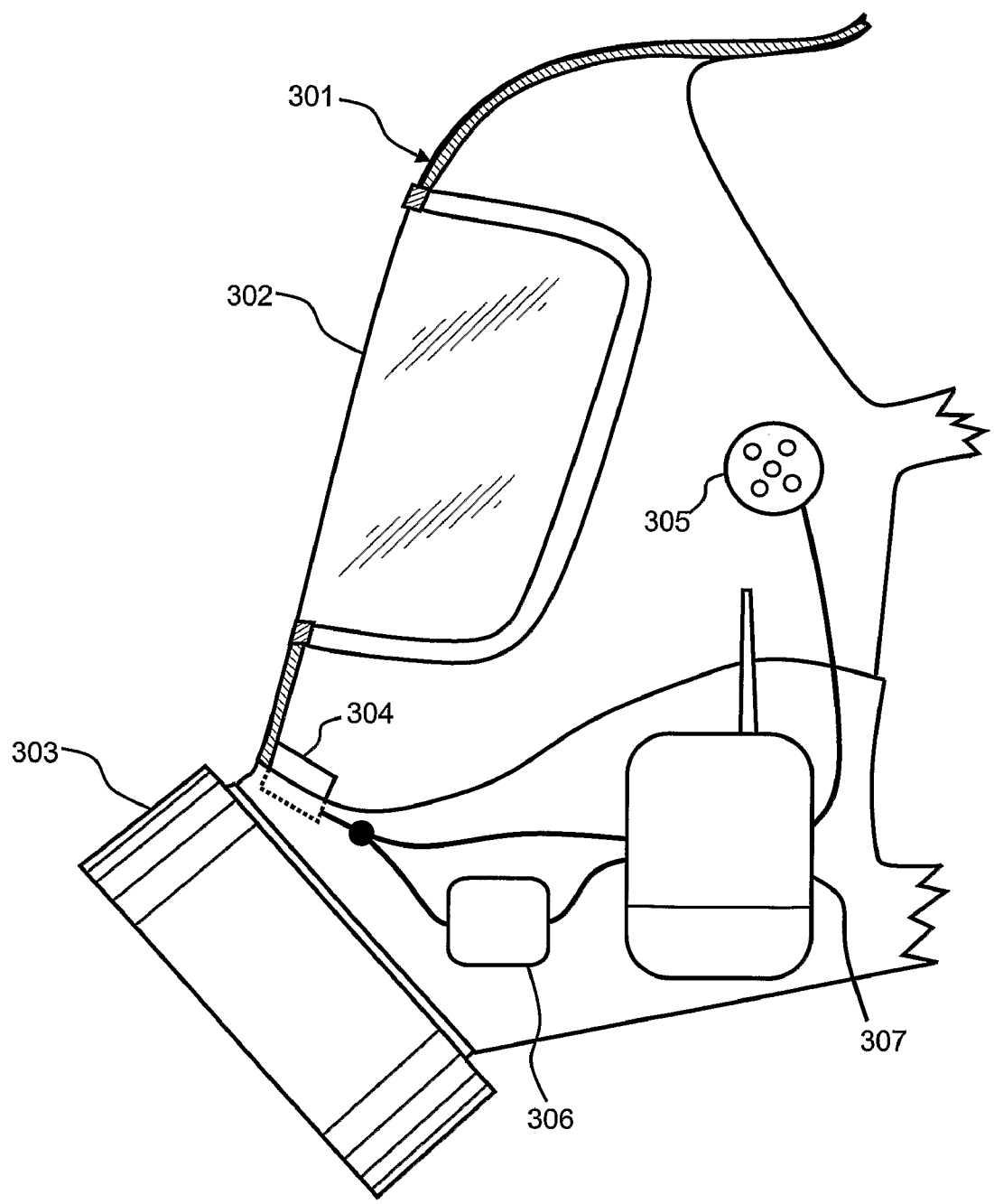
FIG. 3 shows a breathing protection apparatus according to an embodiment of the invention.

FIG. 3 shows a breathing protection apparatus according to an embodiment of the invention. The breathing protection apparatus comprises a breathing mask 301 having an eye shield 302 and a filter element 303 that is arranged to filter the air inhaled by a wearer of the breathing protection apparatus. The breathing mask 301 is shown as a partial section view in FIG. 3. The breathing protection apparatus comprises a radio communication device 307 capable of transmitting a radio signal containing information of an audio signal that is measured in the breathing mask 301 and a control unit 306 arranged to monitor the audio signal and to activate the radio communication device 307 to transmit the above-mentioned radio signal as a response to a situation in which the audio signal is detected to contain speech of a wearer of the breathing protection apparatus. The audio signal is produced with a transducer device 304 that preferably comprises a microphone. The radio communication device 307 is connected to an earphone 305.

A benefit provided by breathing protection apparatus shown in FIG. 3 is that power consumption of the radio communication device 307 can be reduced without a need for manual control actions that could limit the freedom of action of a user of the breathing protection apparatus, e.g. a fire fighter.

In a breathing protection apparatus according to an embodiment of the invention the radio communication device 307 is capable of transmitting another radio signal during a time period in which the radio communication device 307 is not activated to transmit the radio signal containing information of the audio signal. The other radio signal can represent one or more of the following: a test signal for monitoring a radio link, a monitoring signal carrying measured data, and an update signal for a transceiver at a far end of the radio link.

In a breathing protection apparatus according to an embodiment of the invention a transmitter of the radio communication device 307 is arranged to transmit digital data to a radio path and a receiver of the radio communication device 307 is arranged to receive digital data from the radio path. The transmitter can be adapted to use e.g. the quadrature amplitude modulation (QAM) line code or the carrierless amplitude and phase modulation (CAP) line code. Correspondingly, the receiver can be adapted to use e.g. the quadrature amplitude modulation (QAM) line code or the carrierless amplitude and phase modulation (CAP) line code.

In a breathing protection apparatus according to an embodiment of the invention the radio communication device 307 is arranged to support the Bluetooth® data transfer protocol.

In a breathing protection apparatus according to an embodiment of the invention the radio communication device 307 is arranged to support a data transfer protocol of a wireless local area network (WLAN).

In a breathing protection apparatus according to an embodiment of the invention the radio communication device 307 is arranged to support the WiMax data transfer protocol. The WiMax data transfer protocol is described e.g. in the IEEE 802.16 specification.

In a breathing protection apparatus according to an embodiment of the invention the radio communication device 307 is arranged to support both the Bluetooth® data transfer protocol and the data transfer protocol of a wireless local area network (WLAN).

Figure 4:
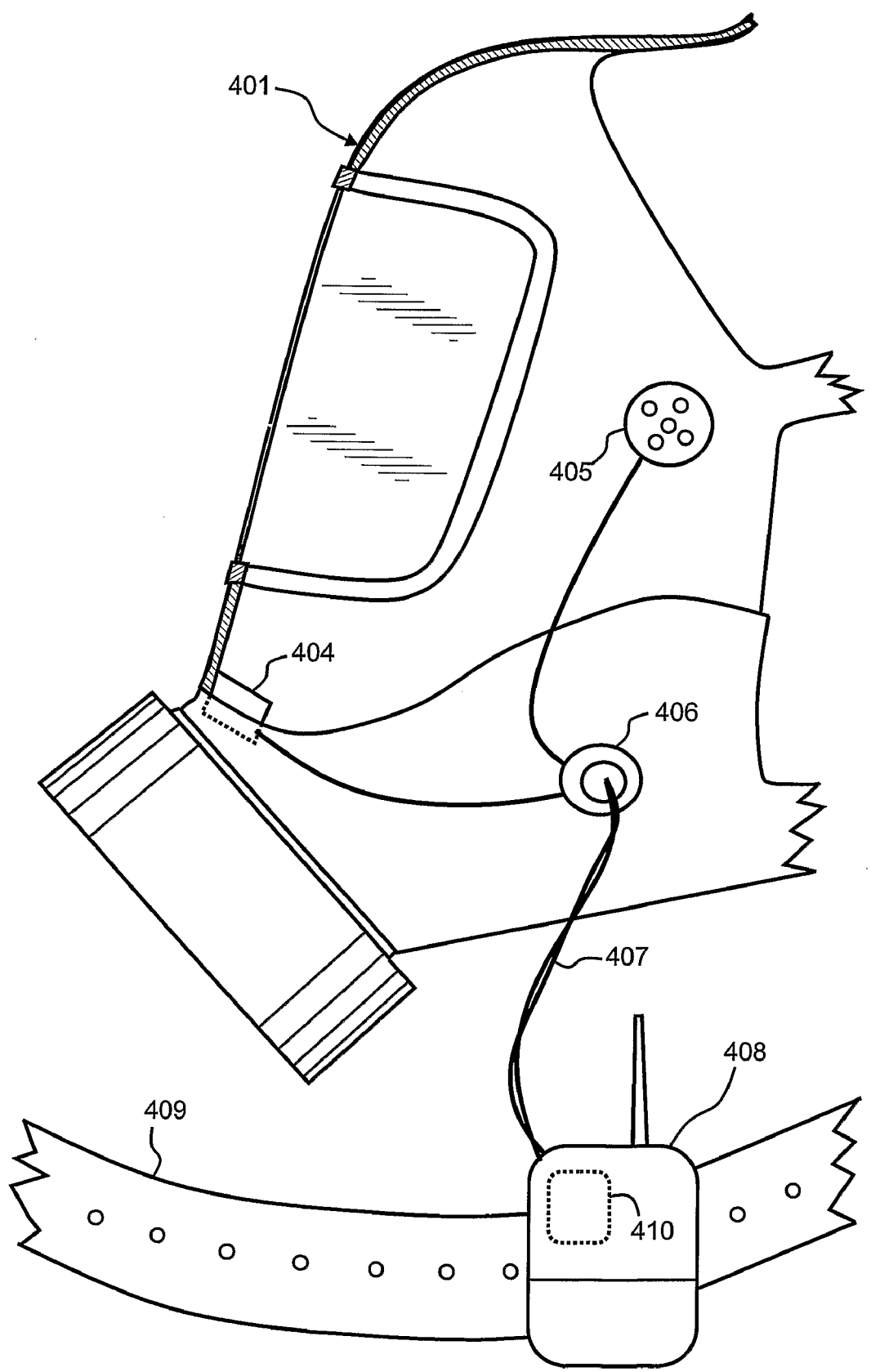
FIG. 4 shows a breathing protection apparatus according to an embodiment of the invention.

In the breathing protection apparatus shown in FIG. 3 the radio communication device 307 and the control unit 306 are physically integrated with the breathing mask 301. An alternative solution for a breathing protection apparatus is shown in FIG. 4. A radio communication device and a control unit 410 are parts of a communication unit 408 that is connected to a breathing mask 401 via a corded link 407. The communication unit 408 can be carried, for example, on a belt 409 of a wearer of the breathing protection apparatus. The corded link 407 and the breathing mask have electrical connectors 406 that can be connected to each other. The breathing mask 401 comprises a microphone 404 and an earphone 405 that are electrically coupled with the electrical connector 406.

Figure 5:
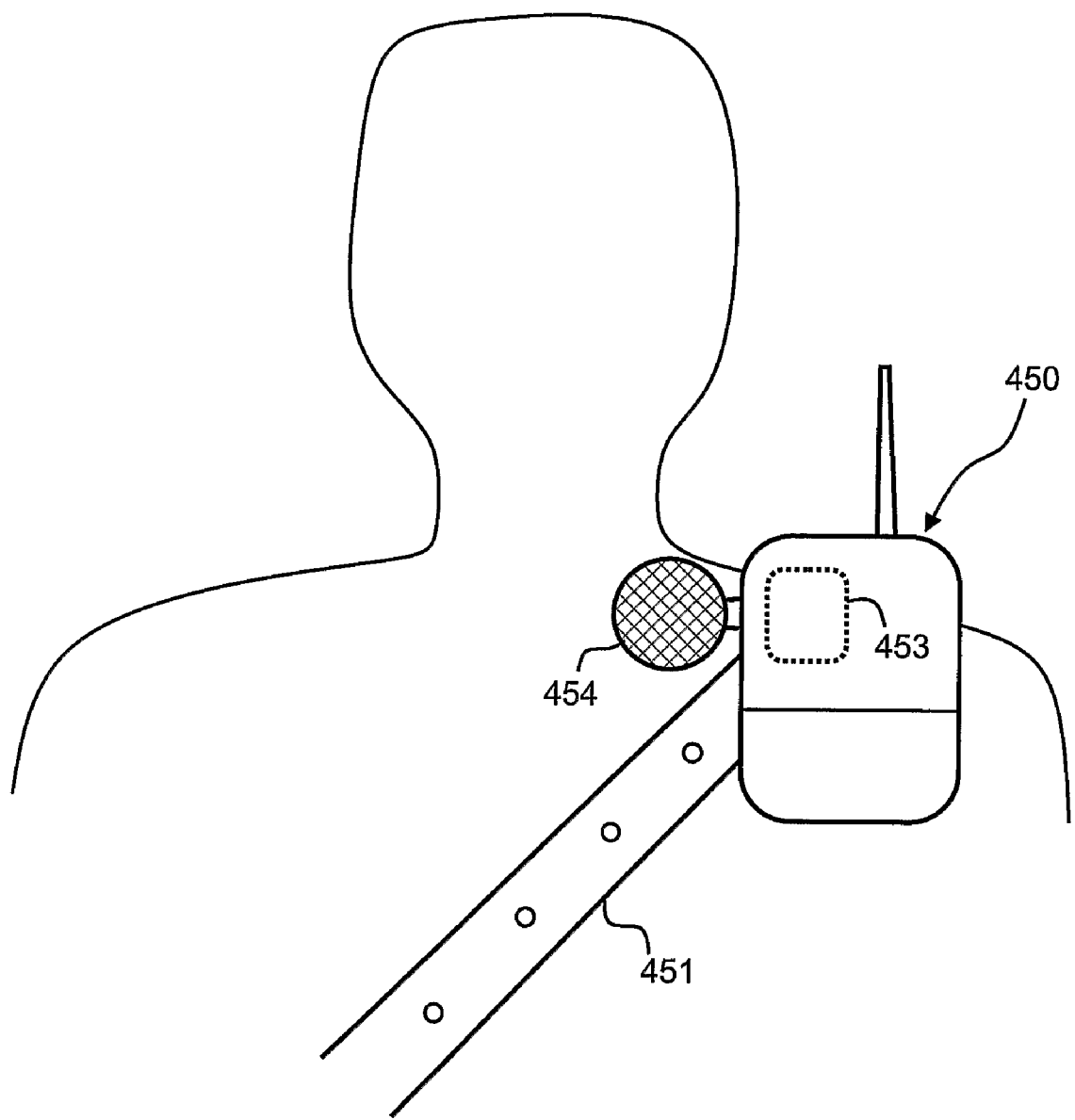
FIG. 5 illustrates a possible way of using a radio communication device according to an embodiment of the invention.

FIG. 5 illustrates a possible way of using a radio communication device according to an embodiment of the invention. The radio communication device 450 is carried on a shoulder belt 451. The radio communication device comprises 450 a microphone 454 arranged to convert voice into an audio signal. The radio communication device comprises a control unit 453 arranged to monitor the audio signal and to activate the radio communication device to transmit a radio signal containing information of the audio signal as a response to a situation in which the audio signal is detected to contain speech.

Figure 6:
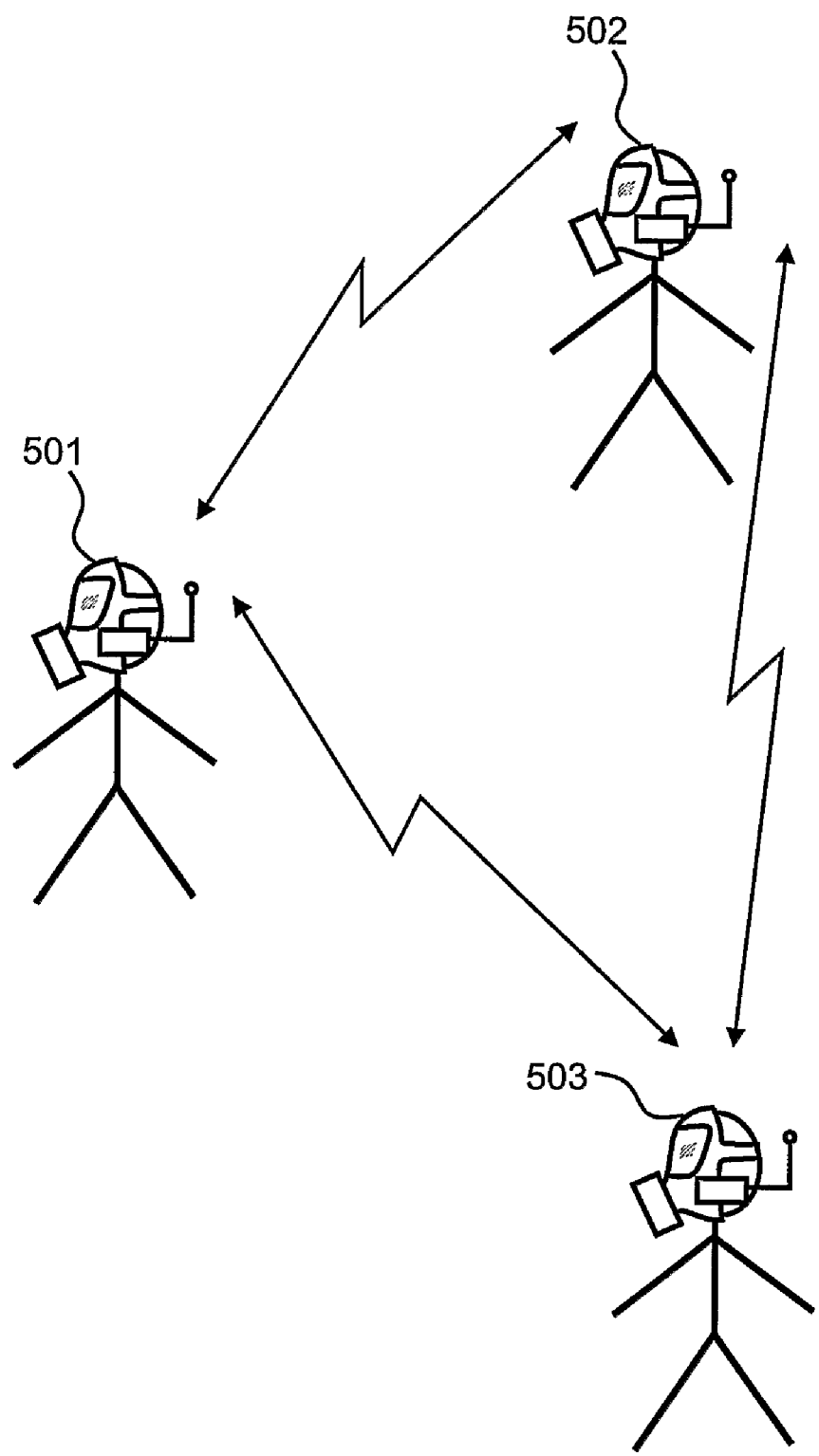
FIGS. 6, 7 and 8 show examples of communication systems comprising one or more radio communication devices according to an embodiment of the invention.
Figure 7:
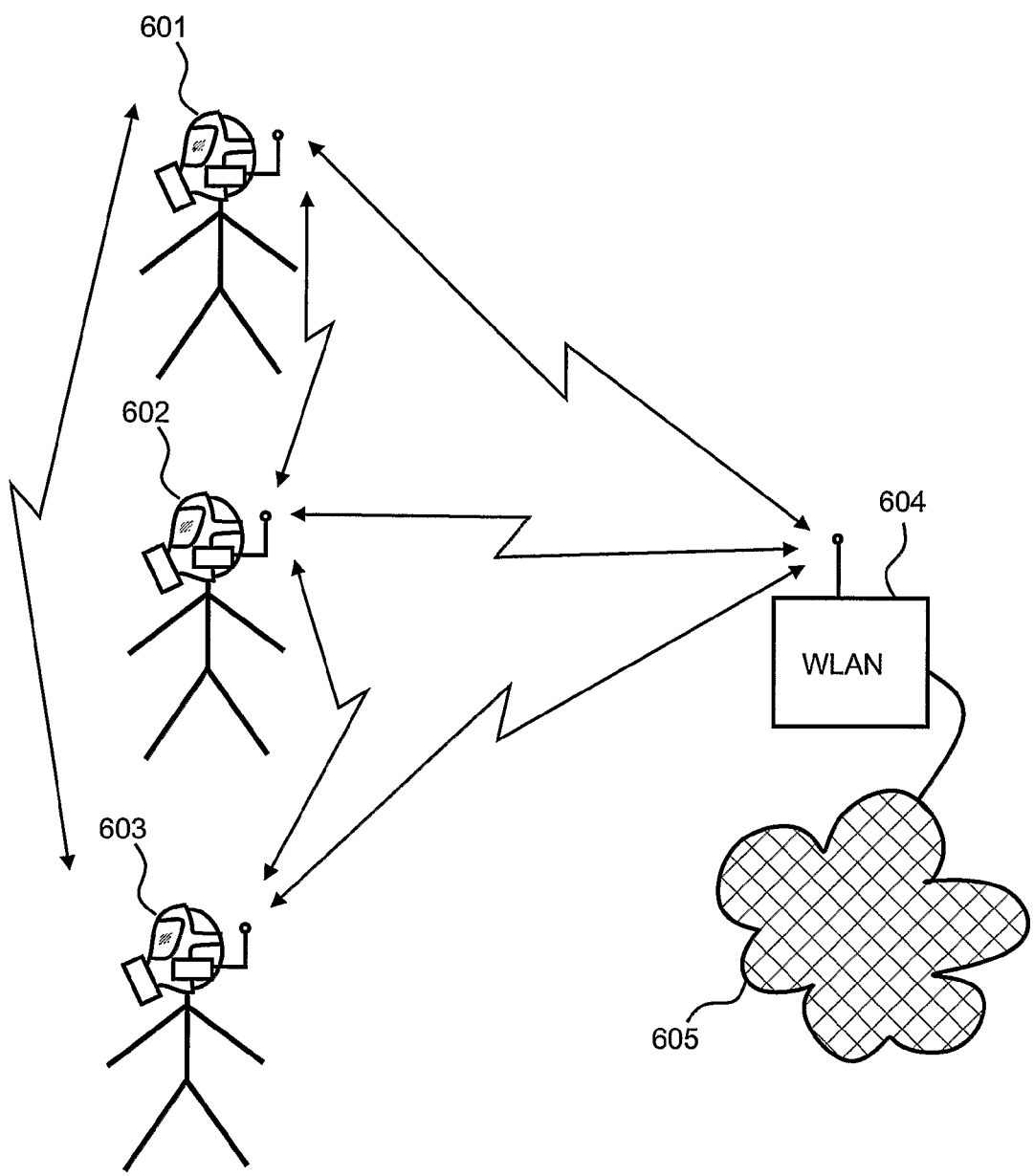
Figure 8:
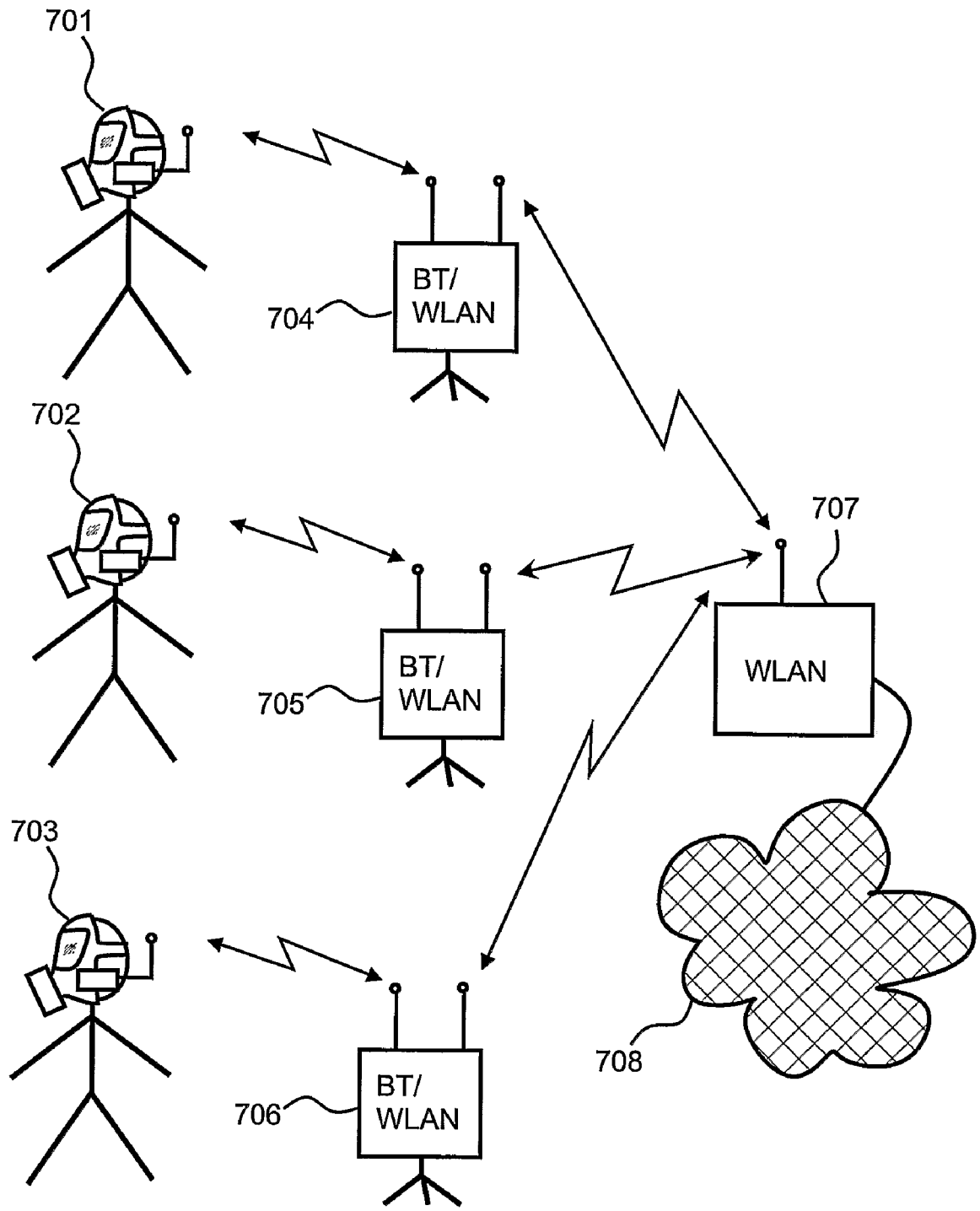

Each of FIGS. 6, 7 and 8 shows an example of a communication system comprising one or more radio communication devices according to an embodiment of the invention. In the examples shown in FIGS. 6, 7, and 8 each radio communication device according to an embodiment of the invention is integrated with a breathing protection apparatus. FIG. 6 shows an example of a communication system in which every breathing protection apparatus 501, 502, and 503 is connected with a radio link to every other breathing protection apparatus (everyone-hears-everyone). FIG. 7 shows an example of a communication system in which every breathing protection apparatus 601, 602, and 603 is connected with a radio link to every other breathing protection apparatus and, in addition, each breathing protection apparatus is connected with a radio link to a base station 604 of a wireless local area network (WLAN). The base station 604 can be connected to a communication network 605 that can be, for example, a local area network (LAN). FIG. 8 shows an example of a communication system in which each breathing protection apparatus 701, 702, 703 is connected with a Bluetooth® radio link to a portable Bluetooth® base station 704, 705, 706. Each portable Bluetooth® base station is connected with a radio link to a base station 707 of a wireless local area network (WLAN). The base station 707 can be connected to a communication network 708. The portable Bluetooth® base stations 704, 705, 706 can be used for extending the maximum operational distance between the breathing protection apparatuses 701, 702, 703 and the base station 707 without a need to increase the radio transmission powers of the breathing protection apparatuses.

Figure 9:
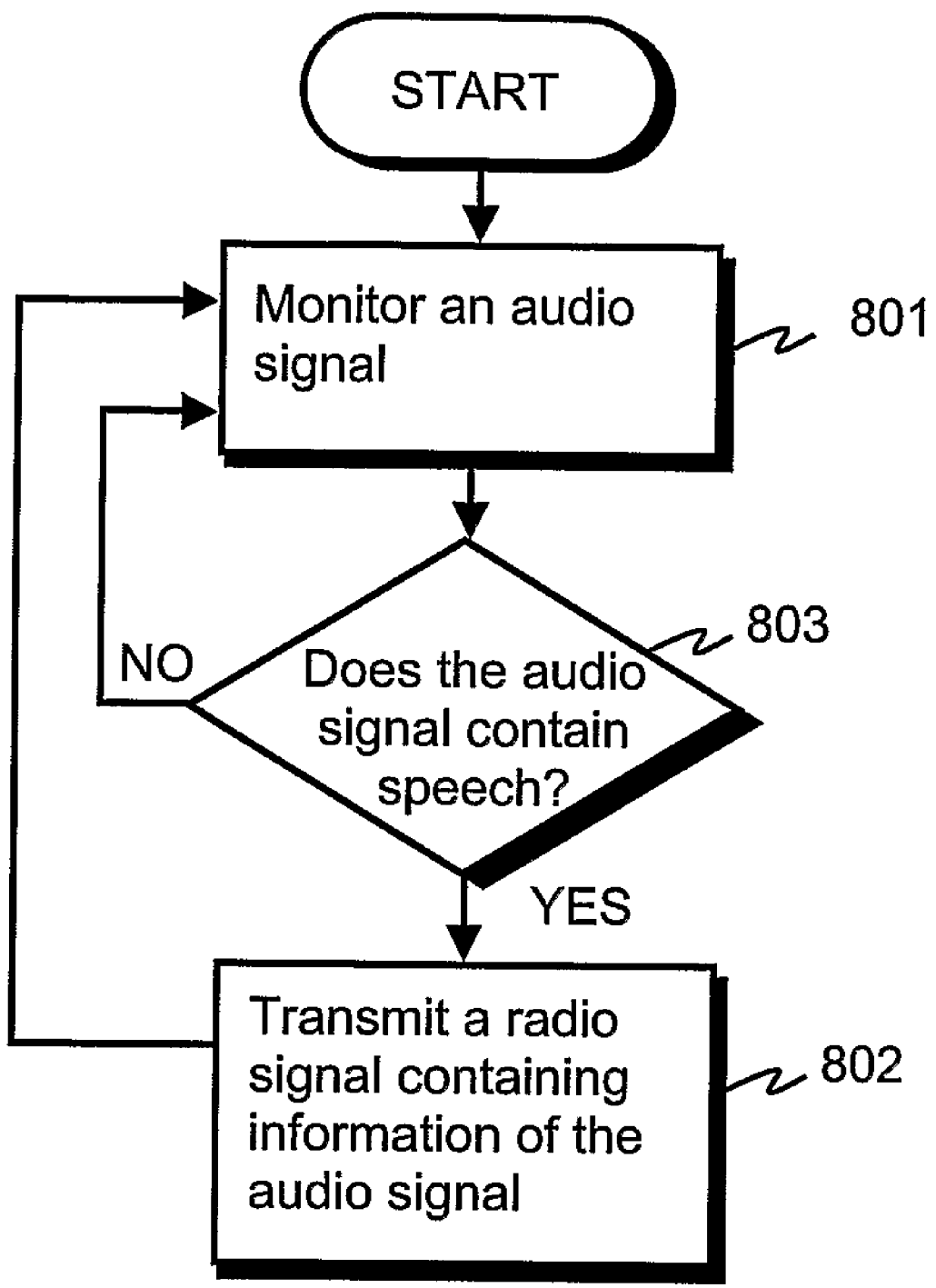
FIG. 9 is a flow chart of a method according to an embodiment of the invention for reducing power consumption of a radio communication device.

FIG. 9 is a flow chart of a method according to an embodiment of the invention for reducing power consumption of a radio communication device. In phase 801 an audio signal is monitored. If the audio signal is detected 803 to contain speech, the radio communication device is activated 802 to transmit a radio signal that contains information of the audio signal.

During a significant portion of time, the audio signal represents only such voice components that are typically useless, e.g. breathing noise, pressurised air ventilation, and external noise. Furthermore, in conjunction with certain radio protocols, the transmission of the above-mentioned useless voice components would cause undesired reservation of protocol units as time slots, data frames, or data packets. The electrical power needed for transmitting the above-mentioned useless voice components is reduced and the undesired reservation of protocol units is at least partly avoided, because the radio communication device is activated to transmit the radio signal containing information of the audio signal only when the audio signal is detected to contain speech.

There are numerous different ways of detecting whether the audio signal contains speech. Some examples will be presented in this document, but any suitable speech detection method or algorithm known to a person skilled in the art can be used.

In a method according to an embodiment of the invention speech is detected with an adaptive speech detector that is taught to recognize at least one component of speech of a user of the radio communication device. The adaptive speech detector can be, for example, a neural network, an adaptive digital filter, or a combination thereof.

In a method according to an embodiment of the invention a processed audio signal is produced by attenuating signal components of the audio signal other than speech and a situation in which level of the processed audio signal exceed a pre-determined threshold value is regarded as a situation in which the audio signal contains speech. The pre-determined threshold value can be for example zero. There are numerous ways of attenuating signal components of the audio signal other than speech. Some examples are presented below, but any suitable method or algorithm known to a person skilled in the art can be used for attenuating the signal components other than speech.

In a method according to an embodiment of the invention a digital noise whitening filter is used for attenuating the signal components of the audio signal other than speech. The audio signal is an input signal of the digital noise whitening filter and a difference between the audio signal and an output signal of the digital noise whitening filter is the processed audio signal from which signal components other than speech have been attenuated.

In a method according to an embodiment of the invention a digital band-pass filter is used for attenuating signal components of the audio signal that locate outside a frequency band of speech. The audio signal is an input signal of the digital band-pass filter and an output signal of the digital band-pass filter is the processed audio signal from which signal components other than speech have been attenuated.

In a method according to an embodiment of the invention a digital noise whitening filter and a digital band-pass filter are used for attenuating the signal components of the audio signal other than speech. The audio signal is an input signal of the digital band-pass filter and an output signal of the digital band-pass filter is an input signal of the digital noise whitening filter. A difference between the output signal of the digital band-pass filter and an output signal of the digital noise whitening filter is the processed audio signal from which signal components other than speech have been attenuated.

In a method according to an embodiment of the invention an analog band-pass filter is used for attenuating signal components of the audio signal that locate outside a frequency band of speech. The audio signal is an input signal of the analog band-pass filter and an output signal of the analog band-pass filter is the processed audio signal from which signal components other than speech have been attenuated.

In a method according to an embodiment of the invention a receiver of the radio communication device is switched to a power saving mode as a response to the situation in which the audio signal is detected to contain speech. In the power saving mode the whole radio receiver can be deactivated or certain pre-determined functions of the receiver can be deactivated in order to reduce the power consumption of the radio receiver.

In a method according to an embodiment of the invention the radio communication device is prevented from transmitting any radio signals during time periods in which speech is not detected from the audio signal. In a method according to an alternative embodiment of the invention the radio communication device is allowed to transmit another radio signal during time periods in which the radio communication device is not activated to transmit the radio signal containing information of the audio signal. The other radio signal can represent, for example, one or more of the following: a test signal for monitoring a radio link, a monitoring signal carrying measured data, and an update signal for a radio transceiver at a far end of the radio link.

While there have been shown and described and pointed out fundamental novel features of the invention as applied to embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the independent claims appended hereto. The specific examples provided in the description given above should not be construed as limiting. Therefore, the invention is not limited merely to the embodiments described above, many variants being possible without departing from the scope of the inventive idea defined in the independent claims.

What is claimed is:

1. A radio communication device comprising a control unit arranged to monitor an audio signal and to activate the radio communication device to transmit a radio signal containing information of said audio signal as a response to a situation in which said audio signal is detected to contain speech, wherein the radio communication device is further arranged to transmit a monitoring signal carrying measured data during time periods in which the radio communication device is not activated to transmit the radio signal containing information of said audio signal;
wherein monitoring a measured temperature from clothing worn by the user.

2. A radio communication device according to claim 1, wherein said control unit is arranged to receive said audio signal from a microphone that is located in a breathing mask of a breathing protection apparatus.

3. A radio communication device according to claim 2, wherein the radio communication device is physically integrated with the breathing mask of the breathing protection apparatus, and receives measured data comprising measured clothing temperature data.

4. A radio communication device according to claim 2, wherein the radio communication device is connected to the breathing mask of the breathing protection apparatus via a corded link.

5. A radio communication device according to claim 1, wherein the radio communication device comprises a radio receiver and the control unit is arranged to switch the radio receiver to a power saving mode as a response to the situation in which said audio signal is detected to contain speech.

6. A radio communication device according to claim 1, wherein a radio transmitter of the radio communication device is arranged to transmit digital data to a radio path and a radio receiver of the radio communication device is arranged to receive digital data from the radio path.

7. A radio communication device according to claim 6, wherein the radio transmitter is adapted to use a line code that is one of the following: quadrature amplitude modulation (QAM) and carrierless amplitude and phase modulation (CAP), and the radio receiver is adapted to use a line code that is one of the following: quadrature amplitude modulation (QAM) and carrierless amplitude and phase modulation (CAP).

8. A radio communication device according to claim 6, wherein the radio communication device is arranged to support the Bluetooth® data transfer protocol.

9. A radio communication device according to claim 6, wherein the radio communication device is arranged to support a data transfer protocol of a wireless local area network (WLAN).

10. A radio communication device according to claim 6, wherein the radio communication device is arranged to support a data transfer protocol described in the IEEE 802.16 specification (Institute of Electrical and Electronics Engineers).

11. A breathing protection apparatus comprising a breathing mask, wherein the breathing protection apparatus further comprises a radio communication device according to claim 1.

12. A method comprising:
monitoring an audio signal,
activating a radio communication device to transmit a radio signal containing information of said audio signal as a response to a situation in which said audio signal is detected to contain speech, and
activating the radio communication device to transmit a monitoring signal carrying measured data during time periods in which the radio communication device is not activated to transmit said radio signal containing information of said audio signal;
Wherein monitoring a measured temperature from clothing worn by the user.

13. A method according to claim 12, wherein the method comprises using an adaptive speech detector that is taught to recognize at least one component of speech of a user of the radio communication device.

14. A method according to claim 13, wherein said adaptive speech detector is one of the following: a neural network and an adaptive digital filter.

15. A method according to claim 12, wherein a processed audio signal is produced by attenuating signal components of said audio signal other than speech and a situation in which level of said processed audio signal exceed a pre-determined threshold value is regarded as the situation in which said audio signal is detected to contain speech.

16. A method according to claim 15, wherein said pre-determined threshold value is zero.

17. A method according to claim 15, wherein a digital noise whitening filter is used for attenuating the signal components of said audio signal other than speech, said audio signal being an input signal of the digital noise whitening filter and a difference between said audio signal and an output signal of the digital noise whitening filter being said processed audio signal.

18. A method according to claim 15, wherein a digital band-pass filter is used for attenuating signal components of the audio signal that locate outside a frequency band of speech, said audio signal being an input signal of the digital band-pass filter and an output signal of the digital band-pass filter being said processed audio signal.

19. A method according to claim 15, wherein an analog band-pass filter is used for attenuating signal components of the audio signal that locate outside a frequency band of speech, said audio signal being an input signal of the analog band-pass filter and an output signal of the analog band-pass filter being said processed audio signal.

20. A method according to claim 12, wherein a receiver of the radio communication device is switched to a power saving mode as a response to the situation in which said audio signal is detected to contain speech.

21. A method of operating a portable radio communication device located with a breathing mask of a user, comprising:
monitoring an audio signal from a user wearing a breathing mask equipped with a radio communication device to detect speech from the user so as to determining a time period in which speech is detected;
during the time period in which speed is detected, activating the radio communication device to transmit a radio signal containing information of said audio signal,
wherein upon completion of transmitting the radio signal, the radio communication device is deactivated for transmitting the radio signal containing information of said audio signal; and
during a time period in which the radio communication device is deactivated for transmitting the radio signal containing information of said audio signal, activating the radio communication device to transmit another radio signal containing measured data;
wherein monitoring a measured temperature from clothing worn by the user, wherein said another radio signal containing measured data includes the measured temperature.

22. A method according to claim 21, comprising the further step of monitoring a measured temperature, wherein the another radio signal containing measured data includes the measured temperature.

23. A method according to claim 21, comprising the further step of monitoring a measured temperature from clothing worn by the user, wherein,
- said another radio signal containing measured data includes the measured temperature,
- the radio signal containing the measured data is sent as a burst signal, and
- upon completion of transmitting the burst signal with the another radio signal, the radio communication device is deactivated.

24. A method according to claim 21, comprising the further step of monitoring a measured temperature from clothing worn by the user, wherein,
- said another radio signal containing measured data includes the measured temperature, and
- upon completion of transmitting the another radio signal, the radio communication device is deactivated.

* * * * *